United States Patent [19]

Kumagai et al.

[11] Patent Number: 5,394,481
[45] Date of Patent: Feb. 28, 1995

[54] LIQUID CRYSTAL PANEL INSPECTION METHOD

[75] Inventors: Ryohei Kumagai; Kaoru Hiiro; Harumi Shimizu; Manabu Oosaka; Tooru Takahashi, all of Tokyo, Japan

[73] Assignee: Ezel Inc, Tokyo, Japan

[21] Appl. No.: 820,925

[22] Filed: Jan. 15, 1992

[30] Foreign Application Priority Data

Jan. 16, 1991 [JP] Japan .................. 3-015878
Jan. 24, 1991 [JP] Japan .................. 3-023935

[51] Int. Cl.⁶ .............. G06K 9/00; G06K 9/48; G06K 9/20
[52] U.S. Cl. ........................ 382/8; 382/21; 382/48
[58] Field of Search ............ 382/48, 8, 21, 22, 41

[56] References Cited

U.S. PATENT DOCUMENTS

| | | | |
|---|---|---|---|
| 3,803,553 | 4/1974 | Nakano et al. | 382/28 |
| 4,213,117 | 7/1980 | Kembo et al. | 382/8 |
| 4,589,139 | 5/1986 | Hada et al. | 382/8 |
| 4,606,065 | 8/1986 | Beg et al. | 382/18 |
| 4,648,053 | 3/1987 | Fridge | 364/551 |
| 4,783,828 | 11/1988 | Sadjadi | 382/21 |
| 4,943,732 | 7/1990 | Economou | 250/572 |
| 4,979,225 | 12/1990 | Tsujiuchi et al. | 382/17 |
| 5,033,099 | 7/1991 | Yamada et al. | 382/21 |
| 5,146,509 | 9/1992 | Hara et al. | 382/8 |
| 5,173,719 | 12/1992 | Taniguchi | 356/394 |
| 5,185,812 | 2/1993 | Yamashita et al. | 382/8 |
| 5,204,617 | 4/1993 | Kumagai | 324/158 R |

FOREIGN PATENT DOCUMENTS

0359838 3/1990 European Pat. Off. .

OTHER PUBLICATIONS

IBM Journal of Research and Development, vol. 29, No. 1, Jan. 1985, New York, N.Y., pp. 73–86.
IEEE Transactions on Pattern Analysis and Machine Intellience, vol. 4, No. 6, Nov. 1982, New York, N.Y. pp. 557–573.
IEEE Transactions on Pattern Analysis and Machine Intelligence, vol. 10, No. 1, Jan. 1988, New York, N.Y. pp. 56–68.
Patent Abstracts of Japan, vol. 13, No. 480, Oct. 1989.
Patent Abstracts of Japan, vol. 13, No. 482, Nov. 1989.
Klima et al., "LCDs vollautomatischh prufen", Feinwerktechnik & Messtechnik, vol. 97, No. 6, Jun. 1989, pp. 257–260.
Nather et al., "Mustererkennung in der Fertigung", Elektronik, vol. 36, No. 22, Oct. 1987, pp. 154–156.

Primary Examiner—Leo H. Boudreau
Assistant Examiner—Michael Cammarata
Attorney, Agent, or Firm—Cushman, Darby & Cushman

[57] ABSTRACT

A method of inspecting a liquid crystal panel and determining the type of defect. Each part of the liquid crystal panel is extracted and inspected by comparison with an extracted reference part. The parts to be inspected may be found based on the location of previously found parts or by examining a plot of the density in the image. Vector data from a part that is known to be defectless is used to extract the reference part. Alternatively, the contour of a reference part may be determined by analyzing the vector data which was obtained for the parts to be inspected. The type of defect is determined by classifying the defective part according to characteristics of the part's image (e.g., brightness of the pixels) as compared with parts having known defects.

7 Claims, 8 Drawing Sheets

LIQUID CRYSTAL PANEL INSPECTION METHOD

BACKGROUND OF THE INVENTION

1. Field of the Invention

The present invention relates to an inspection method for liquid crystal panels which are used to display information in a computer or similar device.

2. Background Information

Due to manufacturing problems, several percent of the liquid crystal panels manufactured are defective. The conventional method for determining whether a display is defective is by eye-inspection. A liquid crystal panel is made up of parts. A defective panel can be identified and the defective parts roughly found by observing the luminosity of the surface of the panel when it has been energized. By observing a defective panel in detail, it can be determined where the defective parts are and how the parts are defective. Eye-inspection is, however, very difficult and time consuming even for a skilled inspector.

The inspection method used for the automatic inspection of IC's may be applied to the inspection of a liquid crystal panel. This method involves pattern matching, whereby images of the item being inspected are compared with a blueprint. In contrast with the appearance of the flat surface of an IC, however, the parts on a liquid crystal panel are thick and rather three-dimensional. This causes the imprecise input of the edges of the parts. Although the apparatus used to input the image of the liquid crystal panel can be adjusted in an attempt to eliminate this imprecision, such imprecisions may none-the-less be inputted due to optical aberrations and light conditions. This imprecision makes it impossible to always identify defective parts by comparison with a template.

SUMMARY OF THE INVENTION

The present invention provides a liquid crystal panel inspection method by which it is possible for an unskilled worker to inspect a liquid crystal panel in a short time. The parts of the liquid crystal panel being inspected are examined to see if they are defective by comparing them with a corresponding reference part. The reference part is a different part in the liquid crystal panel which was selected for comparison.

Vector data starting from a point on a contour of the reference part is first obtained, and the reference part is selected. The starting point coordinate for inspection of new liquid crystal panels and the contour of the reference part are both determined. A reference part is extracted by using this contour, and the parts to be inspected are then examined using the extracted reference part.

The type of defect which is present in a defective part is determined by classifying the distribution of the two-dimensional statistics value for the part according to known two-dimensional statistics values for defective parts.

PREFERRED EMBODIMENTS OF THE PRESENT INVENTION

The selection of the reference part and each part to be inspected can be practiced by the methods below. In the first embodiment, data of a defectless part which is used for extracting a contour is obtained beforehand, and the parts to be inspected are found based on the location of previously found parts. In the second embodiment, the parts to be inspected are found by examining the plot of the densities of the image, and a reference part is determined by analyzing these parts.

Description of the First Embodiment

Hereinafter, an embodiment of the method for inspecting liquid crystal panels of the present invention is described with reference to the attached drawings.

A defectless part is selected as a reference part from a liquid crystal panel which is to be inspected. The reference part is extracted as an image so that images of other parts can be compared to it to determine whether they are defectless.

The reference part is extracted according to vector data for the peripheral of an image of a defectless part which was saved beforehand as vector data. The peripheral is extracted from a predetermined start point on the reference part according to this vector data.

Figure 1:
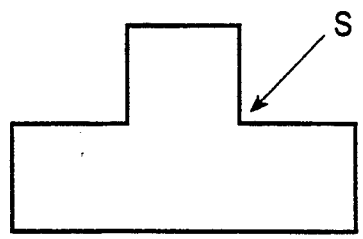
FIG. 1 shows a section of a liquid crystal panel that has a convex corner of a right angle which can be used as a start point for extracting a part.

The contour of a liquid crystal part has generally straight lines, and a precise figure can be reproduced with little data by vectorizing it. A start point is decided and the contour of the part is traced from the start point. An appropriate start point is a characteristic point, such as a convex or concave corner of a relatively large right angle as shown in FIG. 1.

Figure 6:
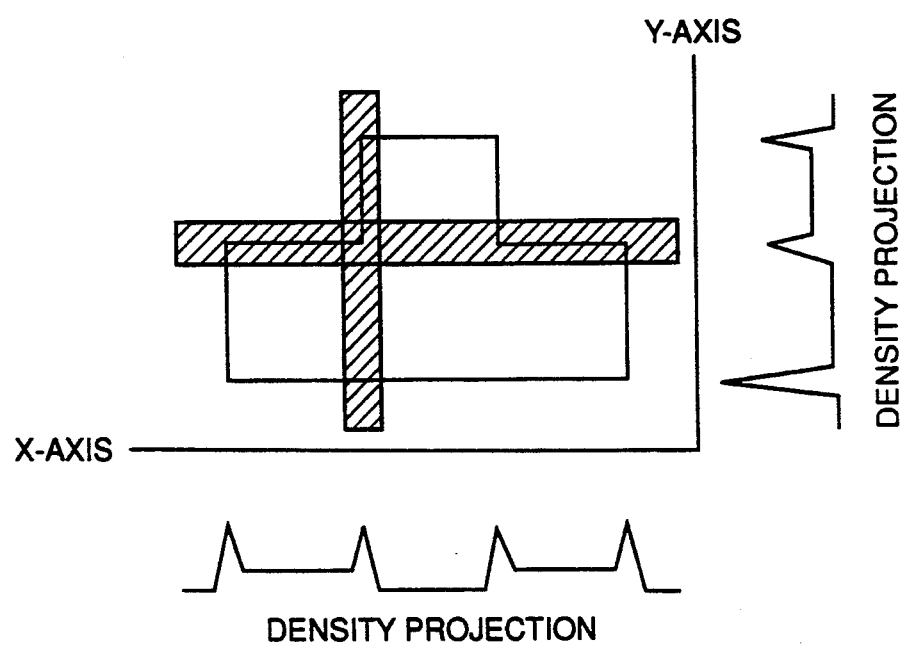
FIG. 6 shows a sample density projection of X-axis and Y-axis using masks.

The convex or concave corner of a right angle can be found by calculating the minimal point of a density projection on a candidate location and the neighboring area (hereinafter "search area") and calculating the minimal point of it. A density projection is a plot of the density of the pixels at each of the X and Y coordinates, as is shown in FIG. 6. The density projection may be performed in the vertical, horizontal and diagonal directions. The location with the most convex or concave corners in the density projection is selected as the convex corner or concave corner.

The candidate locations for the other parts in the liquid crystal panel, which parts will be compared with the reference part, are calculated as follows. Density projection as to differentiated values in an image of multiple parts is performed. The point with the maximal value obtained is a candidate location. Since the liquid crystal parts have substantially the same size and are arranged at constant intervals, the candidate locations for the other parts are searched for at constant intervals from the start point of the maximum density projection of the differential. The size of the search area is determined experimentally.

Figure 2:
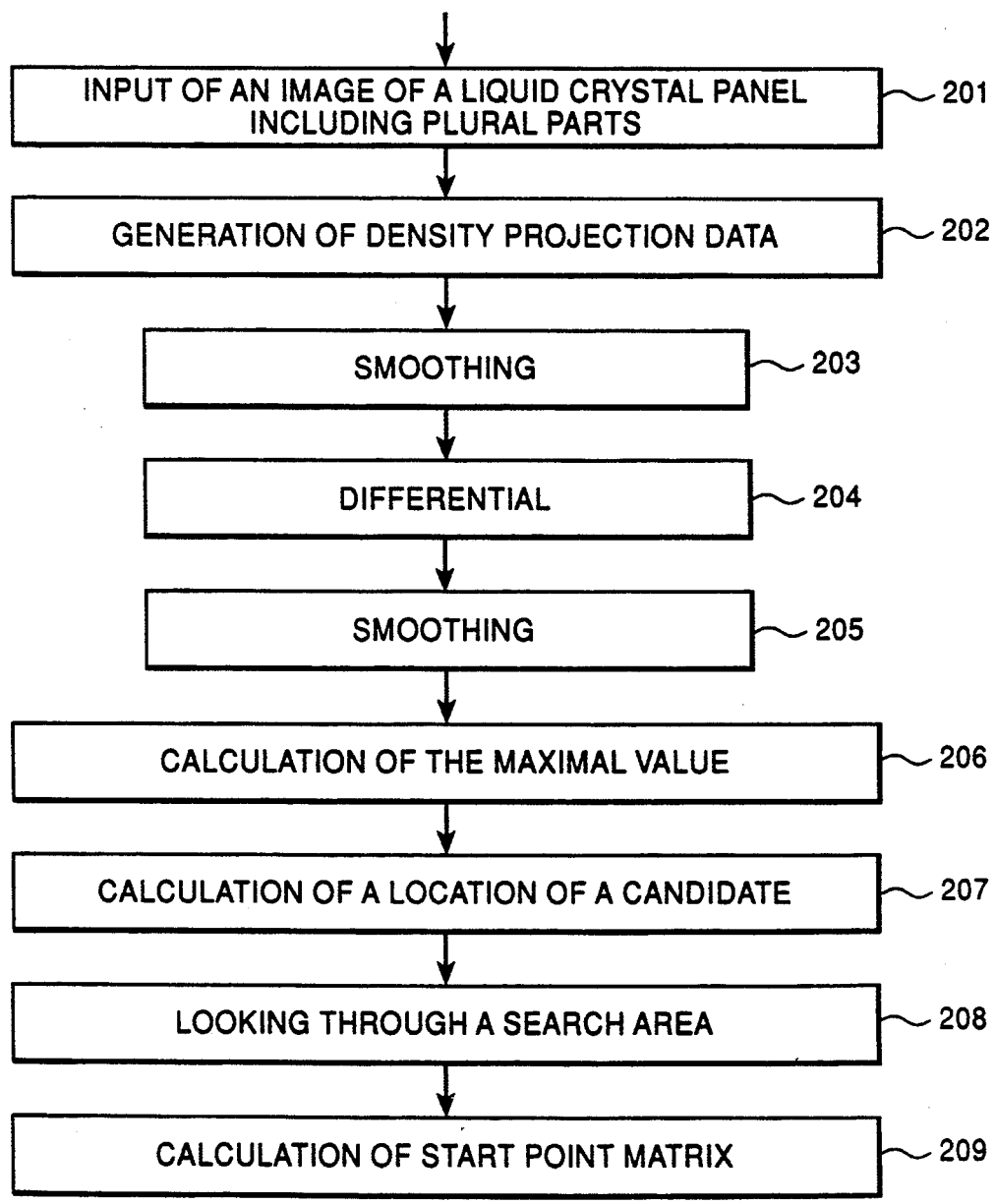
FIG. 2 shows a flow chart which describes the method of a first embodiment of the invention.

The first method will be explained with reference to the flow chart in FIG. 2, which is a flow-chart showing the inspection steps from the input of an image including a plurality of parts to the extraction of the reference image. First, an area which contains multiple parts is inputted as an image in step 201. The size of the area is decided by the process speed of the device and the device's data holding capacity. If a high speed, parallel processing device is used, the size of the area will be governed solely by the data holding capacity of the device.

In step 202, the density projection in the X-direction and Y-direction for the image inputted in step 201 is calculated. As the density projection data probably contains noise, smoothing is performed on the density projection data in step 203. In step 204, the noise reduced density projection data of step 203 is differentiated. The data resulting from step 204 is smoothed for further reduction of noise in step 205. In step 206, the mode (the value occurring most frequently) of the data obtained in step 205 is determined, and it is the coordinates of the mode which define the contour of a part.

Figure 5:
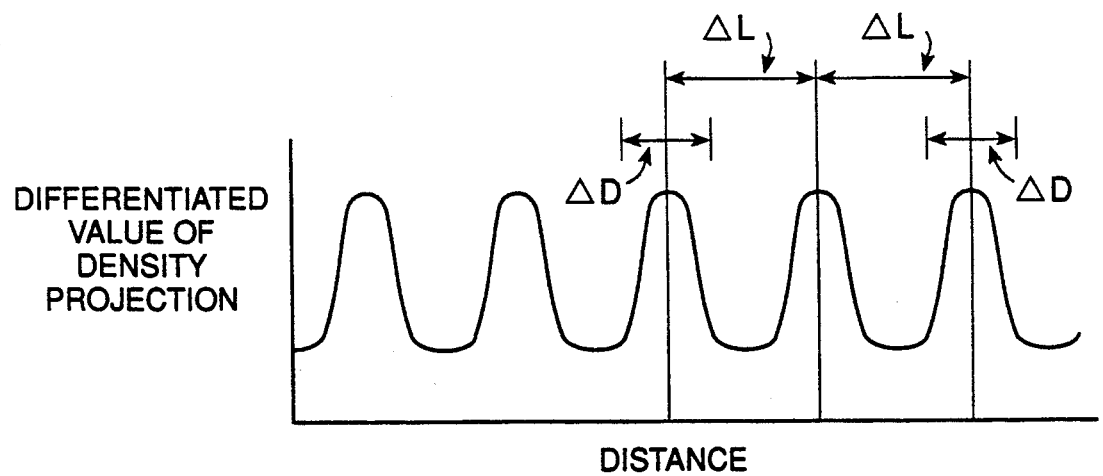
FIG. 5 shows a method for searching a contour.

The parts of the liquid crystal panel are arranged at the same distance $\Delta D$, which distance can be known beforehand. When a contour is found in step 206, other contours are searched starting from the point that defines the first contour in step 207. The other contours are either searched from the startpoint of the first contour or are searched sequentially using the adjacent contour from the startpoint of the first contour. Assuming the contours appear by the distance of $\Delta L$ and the search area is $\Delta D$, the area within the distance from a start point of $\Delta L \pm \Delta D/2$ is searched in step 208. The location with the maximal differential value is judged to be a contour (see FIG. 5), and the start point matrix is calculated based on this point (step 209).

Description of the Second Embodiment

In contrast to the first embodiment, the second embodiment detects the contour of every part and extracts it. Contour's are extracted based on the density change pattern in the gray scale image. As lines of a contour of a part are all horizontal or vertical and are all low density, the minimal value of the density is obtained by tracing the image in the horizontal and vertical directions. Three kinds of patterns are adopted as the patterns of density change which show the minimal value. These are the location of density decrease direction (trough starting point), the location of the minimal density (the middle trough point), and the location of density increase direction (trough ending point).

All of these characteristic points are treated as candidates for specifying a trough, and characteristic points caused by noise are excepted after. The mean density is calculated between an indicative candidate and the next one. Whether an indicative candidate is a true indication is determined by comparing the mean density and the minimal density within the section of the adjacent indicative candidates. Assuming that the mean density is "Dm" the minimal density is "dm" and the coefficient calculated by experience (a constant) is "K", a true trough is found to exist when the following formula is satisfied: $K \times Dm = dm$. This formula will herein be known as "formula (1)".

Figure 3:
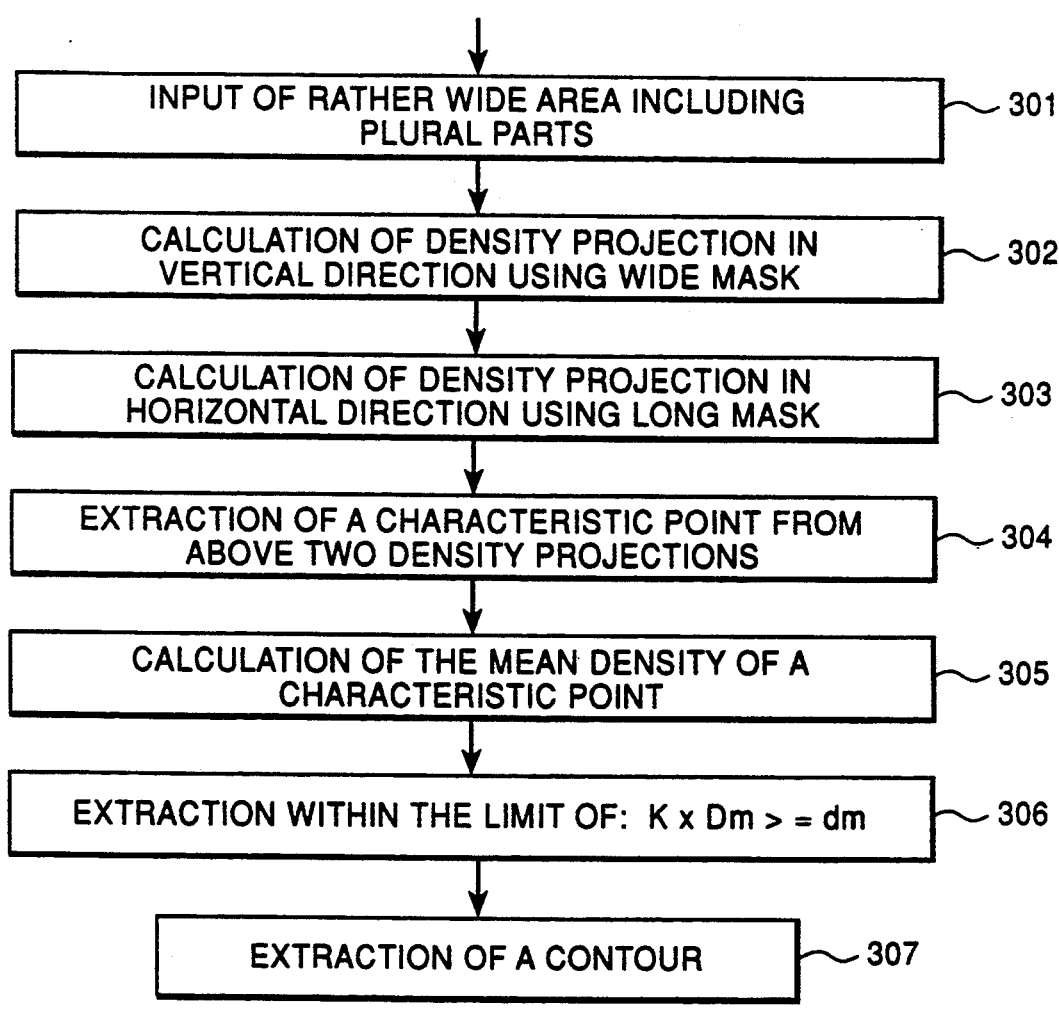
FIG. 3 shows a flow chart which describes the method of a second embodiment of the invention.

FIG. 3 shows the steps of the second method. First, in step 301, an image is inputted in the same way as in step 201 of the first method (see FIG. 2). Density projections in the horizontal and vertical directions are generated for each part in this image, and the contour of a part is then extracted according to the density projection. Density projection in the vertical direction is executed in step 302 and in the horizontal direction in step 303. A horizontal mask is used for the density projection in the horizontal direction and a longitudinal mask is used for the vertical direction, as shown in FIG. 6.

In step 304, the "trough starting point", "middle trough point", and "trough ending point" are calculated and stored. The mean density (Dm) and the minimal density (dm) between the characteristic points are calculated in step 305, and formula (1) is applied in step 306. The true trough is obtained according to the calculation in step 307.

Figure 4:
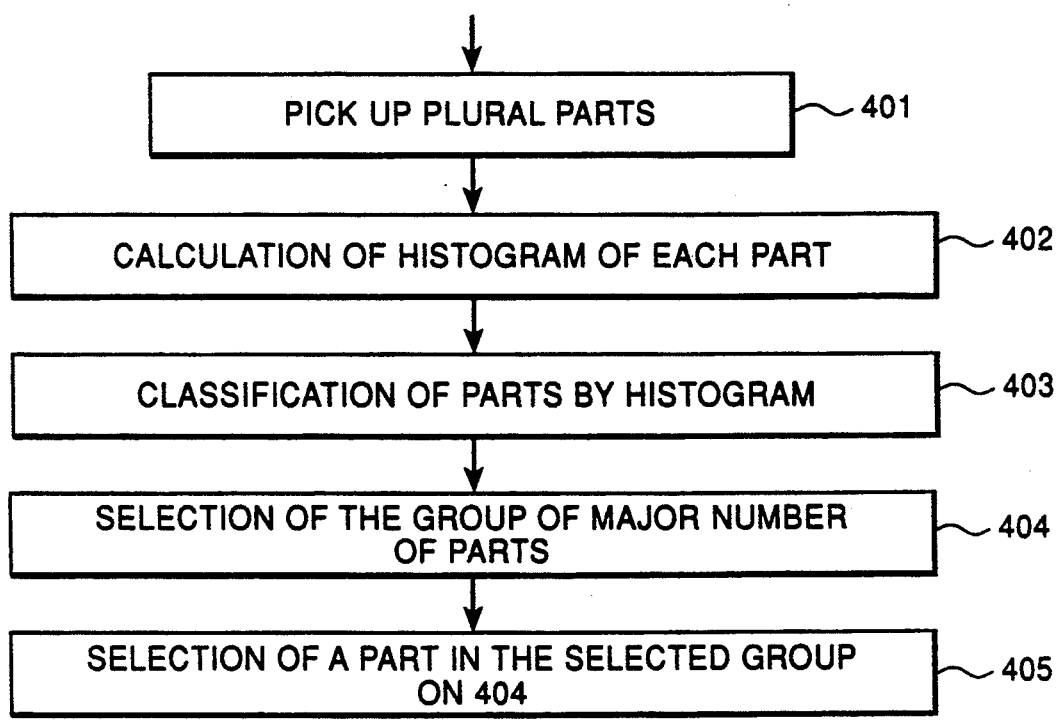
FIG. 4 shows a flow chart which describes a method for extracting a reference part.

Once the parts to be inspected have been found, the reference part can be extracted through the processing described in the flow chart of FIG. 4. First, in step 401 a plurality of parts are extracted by the method mentioned above. The histogram of each part is calculated in step 402. As a histogram is an important characteristic in determining whether a part is defective, normal parts can be extracted by classifying the parts into groups according to the histogram.

Considering the percentage of defective parts of liquid crystal panels, the normal parts probably belong to the group with the largest number of members. Therefore in step 404, parts that fall within the group with the largest number of members are treated as normal parts. A part having the mean density of the pixels in this group is usually selected to be the normal part.

Because the method extracts the contour of a part precisely, it is possible for method 2 to extract a part easily according to vector data when only one point on the contour of a part to be extracted is picked up after generating vector data of the contour. A reference part and other parts are extracted by performing this processing to all parts of a panel to be inspected. A part is determined to be defective by comparing contour of the reference part with the contour of each of the other parts of the liquid crystal panel.

Description of the Third Embodiment

Figure 8:
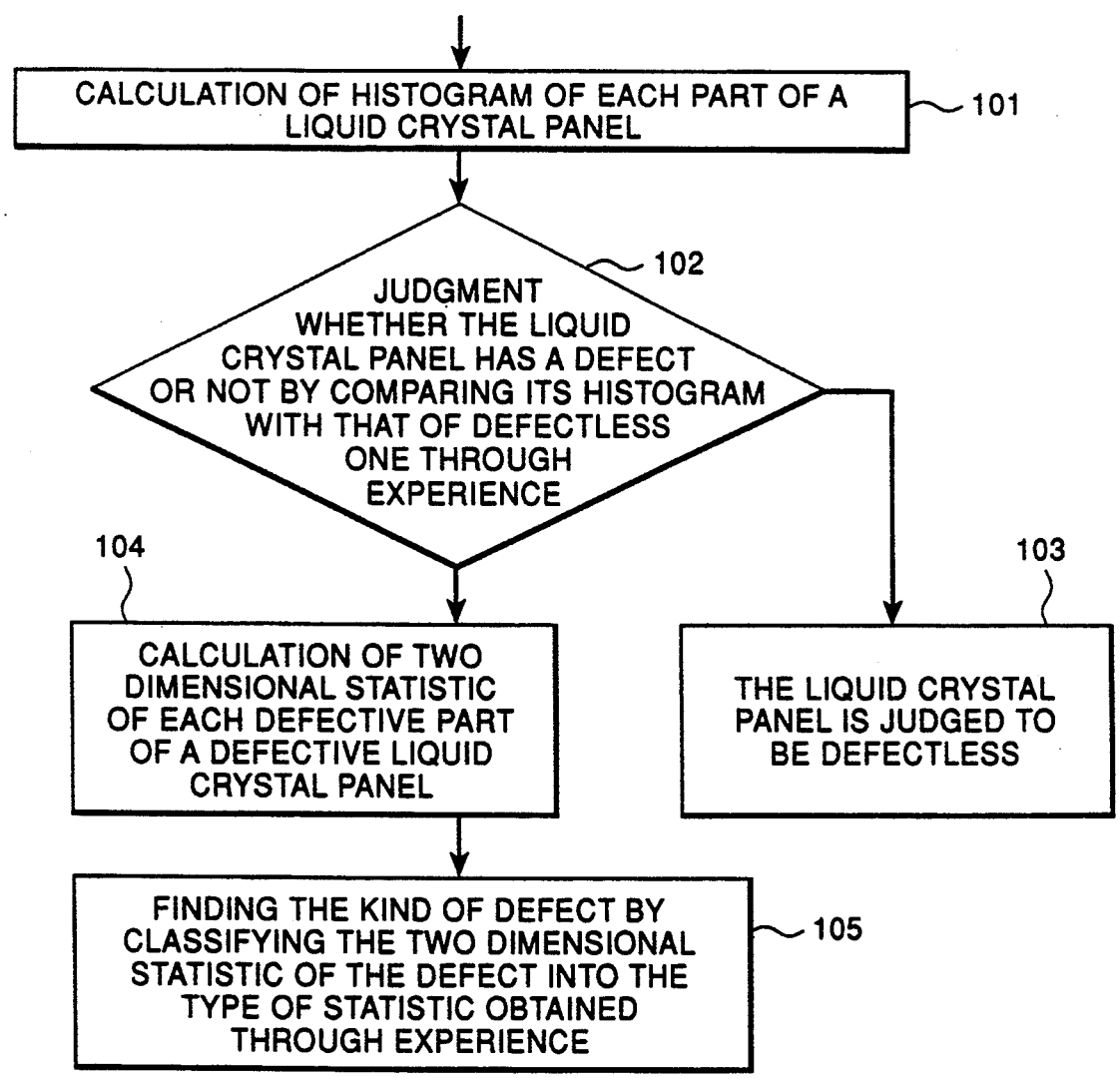
FIG. 8 shows a flow chart which describes a third embodiment of the invention.
Figure 10:
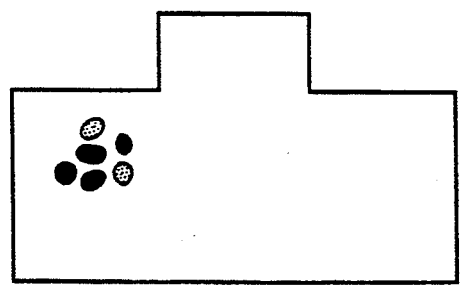
FIG. 10 shows a section of a liquid crystal panel having a spots defect.
Figure 11:
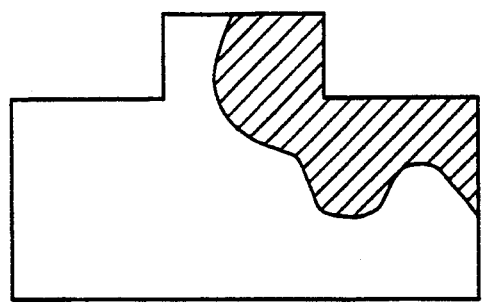
FIG. 11 shows a section of a liquid crystal panel having a blot defect.
Figure 12:
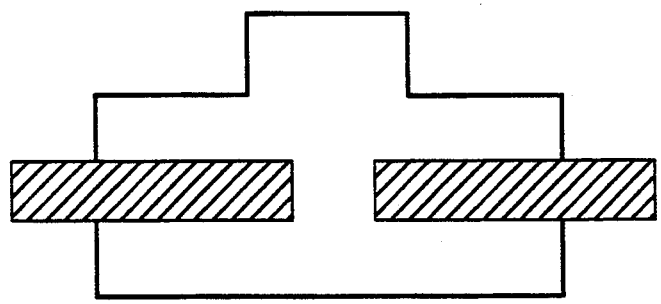
FIG. 12 shows a section of a liquid crystal panel having a break defect.
Figure 13:
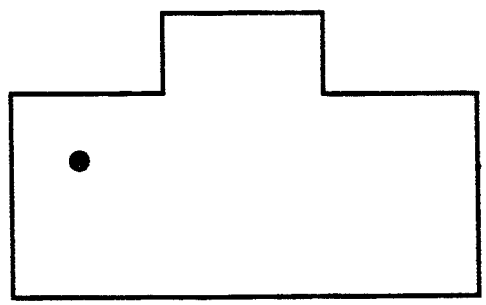
FIG. 13 shows a section of a liquid crystal panel having a pinpoint defect.
Figure 14:
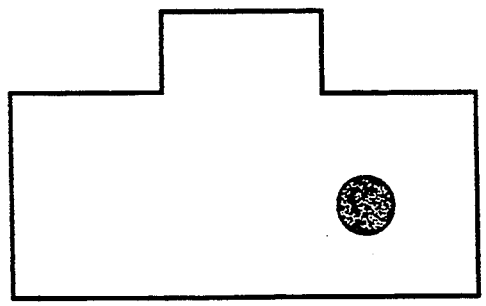
FIG. 14 shows a section of a liquid crystal panel having a hole defect.

The third embodiment of the present invention concerns classifying the type of defect that is found in a liquid crystal panel. The five types of defects that are known to occur in liquid crystal panel parts are the following: i) spots defect (FIG. 10); ii) blot defect (FIG. 11); iii) break defect (FIG. 12); iv) pinpoint defect (FIG. 13); and v) hole defect (FIG. 14). The two dimensional statistics value for the above-mentioned known defects are used by the third embodiment as discussed below with reference to FIG. 8.

The image of each part of a liquid crystal panel to be inspected is inputted by a camera and the histogram of the image is determined in step 101. The histogram is compared with that of a defectless part in step 102. By this comparison, it is possible to determine if a defective part exists in the liquid crystal panel being inspected. If the liquid crystal panel being inspected is determined not to have defects, it is found to be a good panel in step 103. On the hand, if it is determined that the liquid crystal panel has defects then it will be further inspected to determine what kind of defect exists in it.

As is mentioned above, there are five types of defects. It is clear by experience that for each type of defect there is a characteristic distribution of the two dimensional statistics value of the histogram. Thus, after calculating the two dimensional statistics value of the histogram of a defective part in step 104, it is possible in step 105 to determine the type of the defect according to the area of the histogram where the calculated value is located.

In this case, the representative density and variance are used as the two dimensional statistics value. The mean value or the middle value are used as the representative density.

Figure 9:
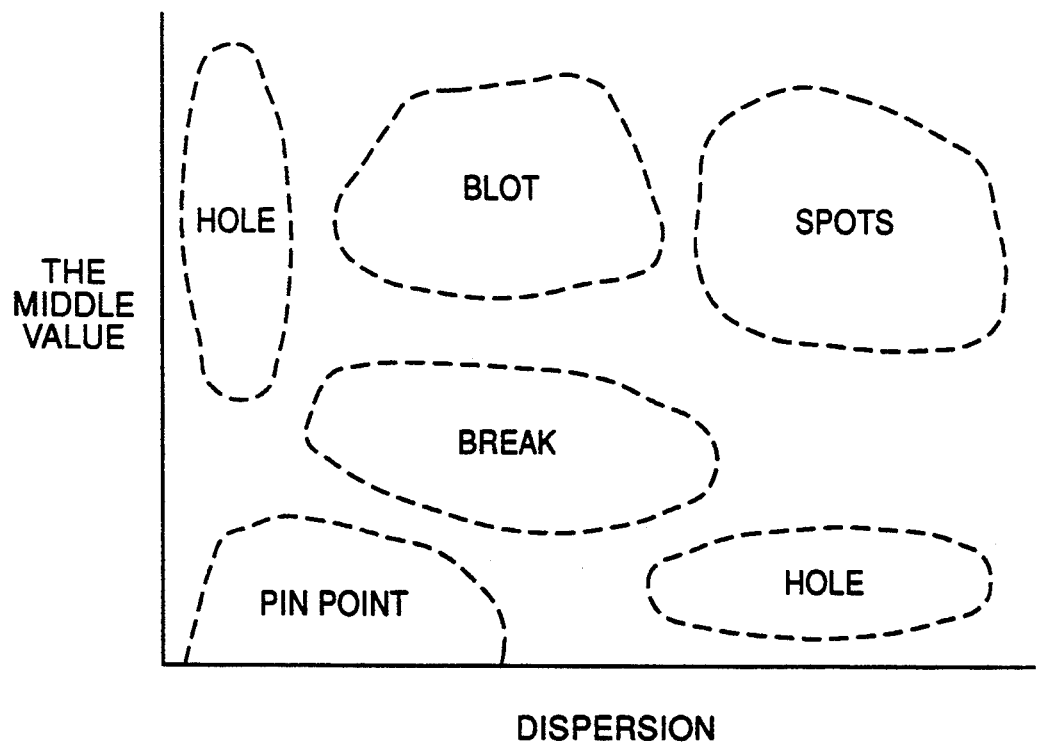
FIG. 9 shows the different types of defects according to their two dimensional statistics value and variance.

The distribution of the two dimensional statistics value are shown in FIG. 9. Usually, each part of a liquid crystal panel has the same shape and is made of the same material. Therefore, when an image of a part is inputted by a camera and the histogram of the image is calculated, pixels of a normal part have a similar brightness.

The distribution of the brightness for a defective part will have a peak, however, and will be different from that of the normal part. For example, when a spot-type defect exists on a part, the brightness has wide variance because the brightness on the area of the defect makes a large difference. On the other hand, when a pinpoint defect exists on a part, the brightness on the area of the defect makes a small variance because it converges on a value.

The brightness for a part containing a blot or break defect is little different from that of a normal part. The distribution shows a peak which is neighboring to the peak of the histogram of a normal part. The variance of parts with blot or break defects is larger than that of a hole defect and smaller than that of a spot defect. Though there is little difference between the variance for a blot defect and a break defect, the middle value for a blot defect is larger than that for a break defect.

When the existent defect is a hole, the two-dimensional statistics value has two areas of variance.

Figure 7:
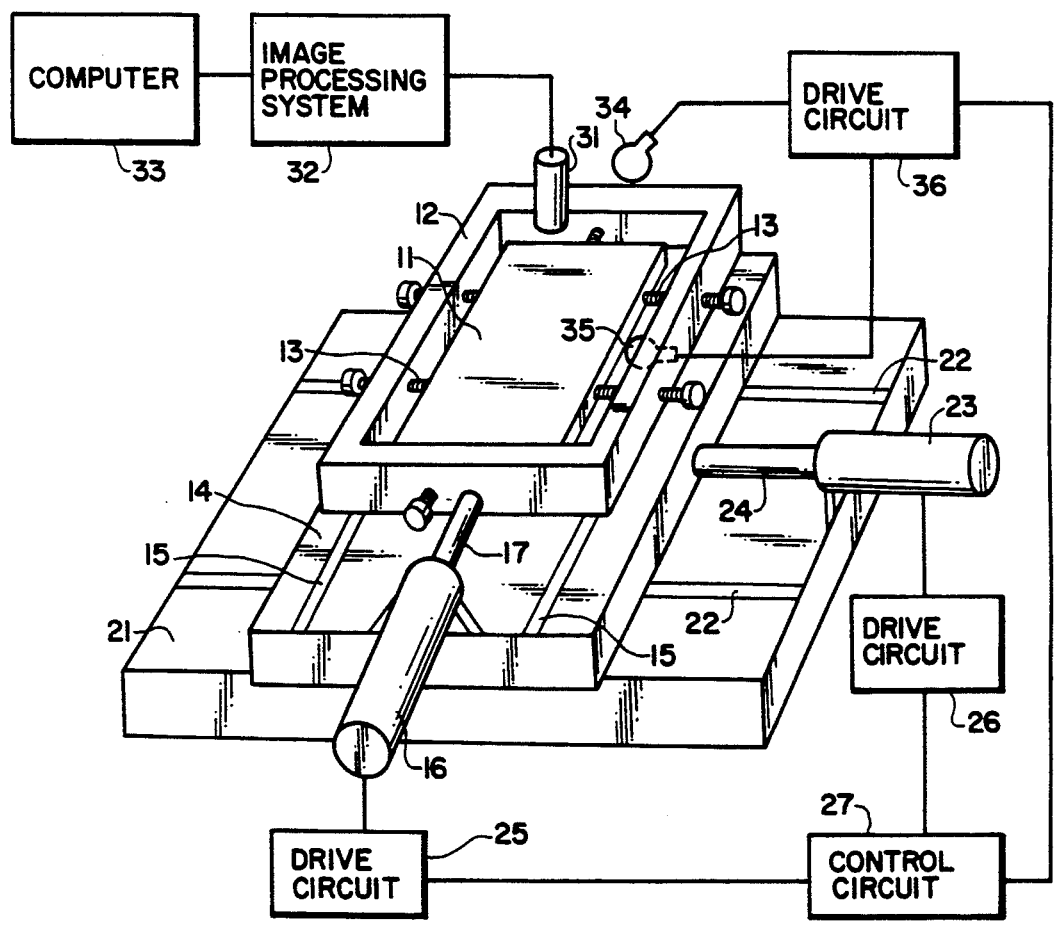
FIG. 7 shows a perspective view of an apparatus used for the inspection method of this invention.

FIG. 7 shows an apparatus used for the present invention. A liquid crystal panel 11 is located inside of a support frame 12 so as to be fixed on the frame 12 with bolts 13. Support frame 12 is movably mounted on a pair of rails 15 on a movable plate 14. A cylinder device 16 is fixed on the end of movable plate 14, whose piston rod 17 is connected with the support frame 12. Movable plate 14 is movably mounted on a pair of rails 22 on fixed plate 21. Just as with movable plate 14, the fixed plate 21 is provided with a cylinder device 23 at one end whose piston rod 24 is connected with the movable plate 14.

Support frame 12 is moved in parallel to movable frame 14 by controlling cylinder device 16, and movable plate 14 moves in parallel to fixed plate 21 by controlling cylinder device 23. Cylinder devices 16 and 23 are driven by drive circuits 25 and 26, respectively, so as to move the piston rods 17 and 24 forward or backward. Drive circuits 25 and 26 controlled by a control circuit 27.

A microscope 31 is supported by a fixed frame (not shown) above the liquid crystal panel 11. Each pattern is inputted through the microscope 31, as described later. The image of this pattern is inputted to image processing system 32 and various processings are performed therein. Image processing system 32 is controlled by computer 33.

A light source 34, such as a stroboscope, is provided for lighting the support frame 12 above. It is fixed to support frame 12 and move with it. Light source 34 is driven by a drive circuit 36 which is controlled by control circuit 27.

As mentioned above, the present invention makes it possible for an unskilled worker to precisely inspect the whole of a liquid crystal panel in a short time and to identify defective parts and classify the type of defect found.

What is claimed is:

1. A method of inspecting a liquid crystal panel for defects, comprising the steps of:
   i) inputting an image of a single liquid crystal panel wherein said liquid crystal panel contains parts;
   ii) generating density projection data for said image of said liquid crystal panel;
   iii) selecting a single defectless one of said liquid crystal panel parts as a single reference part and determining a vectorization starting point on said single reference part using said density projection data;
   iv) generating a vectorized contour of said single reference part using said vectorization starting point; and
   v) examining all other parts in said liquid crystal panel, which are to be inspected, by making a comparison with said single reference part based on said vectorized contour to determine which of said all other parts are defective.

2. A method of inspecting a liquid crystal panel for defects, comprising the steps of:
   i) inputting an image of a liquid crystal panel, wherein said liquid crystal panel contains parts;
   ii) selecting a defectless one of said liquid crystal panel parts as a reference part and determining a vectorization starting point on said reference part;
   iii) generating a contour of said reference part using said vectorization starting point; and
   iv) examining all other parts in said liquid crystal panel, which are to be inspected, by making a comparison with said reference part based on said contour, where in said examination includes the following steps:
      iv$_a$) generating density projection data for said image of said liquid crystal panel;
      iv$_b$) differentiating said density projection data;
      iv$_c$) defining the following three points as candidates for being edges of a part:
         a) a point on which said differentiated data changes from 0 to minus;
         b) a point on which said differentiated data changes from plus to 0; and
         c) a point on which said differentiated data changes from minus to plus;
      iv$_d$) calculating the mean density between said points which are adjacent to each other;
      iv$_e$) defining a threshold for each said point to be a predetermined value multiplied by said mean density; and
      iv$_f$) defining, for each said point, said point to be an edge of a part when said density projection value for said point is less than or equal to said threshold for that point.

3. The method of claim 1, wherein step v) comprises the step of finding coordinates for each said other part by searching an area which is within a tolerance of a predetermined distance from said single reference part.

4. The method of claim 1, wherein step iii) includes the steps of:
- iii$_a$) extracting, from said image of said liquid crystal panel, the vectorized contours of each said part;
- iii$_b$) creating a histogram for each said part based upon the extracted contours;
- iii$_c$) classifying said parts into groups based on their histogram; and
- iii$_d$) selecting, as said single reference part, a part from said group having the most members.

5. The method of claim 4, wherein step ii$_d$) includes the steps of:
- iii$_{d1}$) calculating a mean density from said histograms;
- iii$_{d2}$) selecting, as said single reference part, a part which has said mean density from said group having the most members.

6. A method of inspecting a liquid crystal panel for defects, comprising the steps of:
- i) inputting an image of a liquid crystal panel, wherein said liquid crystal panel contains parts;
- ii) selecting a defectless one of said liquid crystal panel parts as a reference part and determining a vectorization starting point on said reference part, wherein said determination of said vectorization starting point includes the following steps:
  - ii$_a$) generating density projection data for said image of said liquid crystal panel;
  - ii$_b$) differentiating said density projection data;
  - ii$_c$) selecting a minimum value from said differentiated density projection data;
  - ii$_d$) using said minimal value to define a vectorization starting point corresponding to a reference part.
- iii) generating a contour of said reference part using said vectorization starting point; and
- iv) examining all other parts in said liquid crystal panel, which are to be inspected, by making a comparison with said reference part based on said contour.

7. The method of claim 2, wherein density projection data is generated along a diagonal contour line.

* * * * *